United States Patent [19]
Huffman

[11] Patent Number: 5,868,569
[45] Date of Patent: *Feb. 9, 1999

[54] DENTAL MODEL CAST MOUNTING BLOCK

[75] Inventor: Ronald E. Huffman, Sapulpa, Okla.

[73] Assignee: Dentsply Research & Development Corp., Carlsbad, Calif.

[ * ] Notice: The terminal 11 months of this patent has been disclaimed.

[21] Appl. No.: 467,448

[22] Filed: Jun. 6, 1995

[51] Int. Cl.[6] ................................................. A61C 11/00
[52] U.S. Cl. ................................................. 433/60; 433/64
[58] Field of Search ................................ 433/54, 57, 60, 433/62, 64

[56] References Cited

U.S. PATENT DOCUMENTS

| | | | |
|---|---|---|---|
| D. 306,206 | 2/1990 | Huffman | D24/10 |
| 1,055,357 | 3/1913 | Robin . | |
| 3,092,909 | 6/1963 | Miller | 32/32 |
| 3,808,689 | 5/1974 | Spinella | 326/132 |
| 4,103,424 | 8/1978 | Benjamin et al. | 32/32 |
| 4,299,570 | 11/1981 | Yogosawa | 433/62 |
| 4,382,787 | 5/1983 | Huffman | 433/64 |
| 4,449,930 | 5/1984 | Huffman | 433/64 |
| 4,496,320 | 1/1985 | Hwang et al. | 433/60 |
| 4,533,323 | 8/1985 | Huffman | 433/60 |
| 4,715,815 | 12/1987 | Rossner | 433/64 X |
| 4,734,033 | 3/1988 | Huffman | 433/64 |
| 4,865,544 | 9/1989 | Scruggs | 433/64 |
| 5,046,949 | 9/1991 | Richardson | 433/57 |

*Primary Examiner*—Nicholas D. Lucchesi
*Attorney, Agent, or Firm*—Douglas J. Hura; James B. Bieber

[57] ABSTRACT

A dental articulator structure for use in registration of a pair of casts of a dental model which are positioned in an opposing and spaced relationship. The articulator structure includes at least one axially rigid support member having opposing ends from which multi-piece cast attachment members may be orthogonally attached. The at least one axially rigid support member and the orthogonally attachable cast attachment members being an articulator structure that locates the axially rigid support member substantially close to the back molar face of the opposing pair of dental model casts such that confronting translational movement of the dental model casts is prevented in a plane parallel to the axially rigid support member, especially confronting translational movement in a region where back molars may be missing in a dental model. The multi-piece cast attachment structure is formed having mating curved, partially spherical, surfaces that facilitate multi-directional alignment of the pair of opposing dental model casts. The multi-piece cast attachment structure may be formed as a tandem arrangement that includes a two-piece attachable alignment structure in combination with at least one spacer block that compensates for cast size differences and is attachable to the back face of a selected cast. In a preferred embodiment, the at least one axially rigid support member is formed as a U-shaped structure defining a pair of axially rigid support arms.

3 Claims, 3 Drawing Sheets

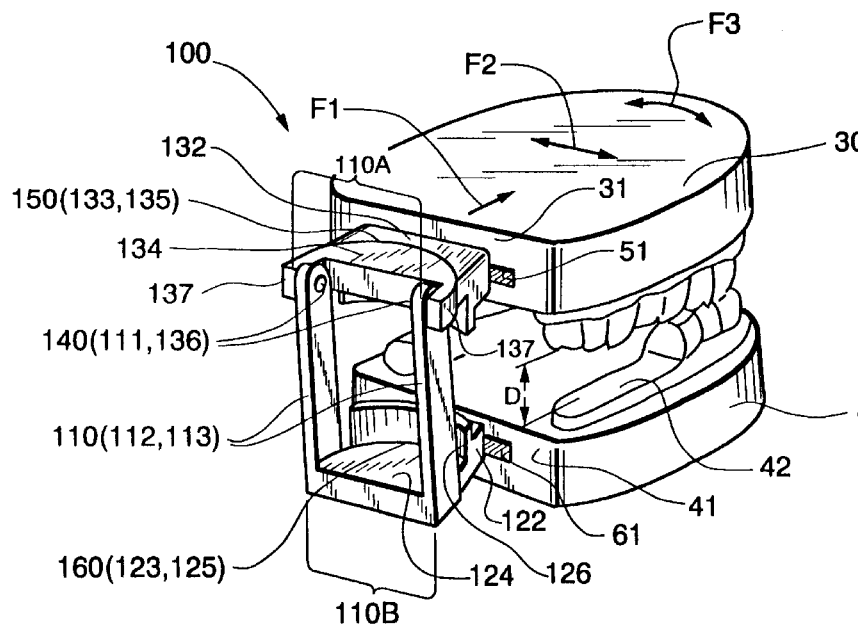
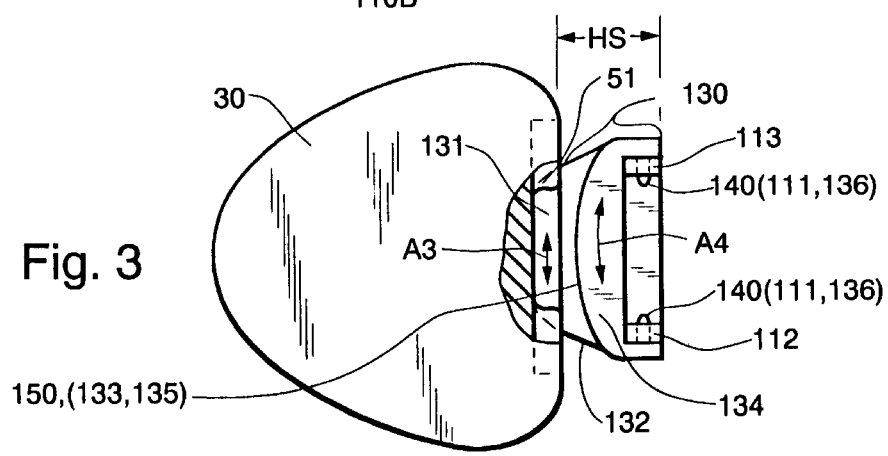
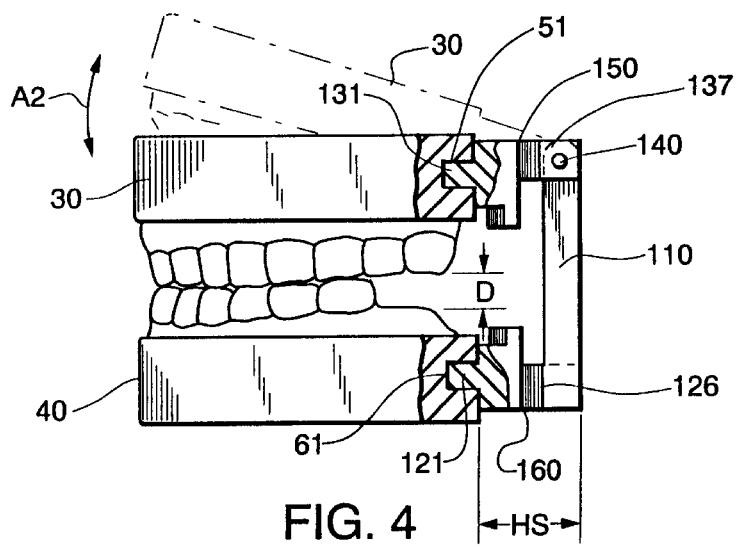

DENTAL MODEL CAST MOUNTING BLOCK

RELATED APPLICATIONS

This application is related to U.S. patent applications being filed on the same date by the same inventor entitled: "VERTICALLY RIGID DENTAL ARTICULATOR SYSTEM AND METHOD", having Ser. No. 08/467,450 filed on Jun. 6, 1995, "SPACER BLOCK FOR A DENTAL ARTICULATOR", having Ser. No. 08/467,453 filed on Jun. 6, 1995, and "VERTICALLY STABLE ARTICULATOR HAVING DUAL STRUTS", having Ser. No. 08/466,731 filed on Jun. 6, 1995.

FIELD OF THE INVENTION

This invention relates to dental articulators. More particularly, the present invention relates to dental articulators for use in registration of dental model casts positioned in opposing and spaced relationship. Even more particularly, the present invention relates to dental articulators, for use in registration of dental model casts having non-uniform bite in a molar region of the dental model.

DESCRIPTION OF THE PRIOR ART

Dental articulators are devices used to simulate occlusal and masticatory motion in dental prostheses that are unique to a particular person. In particular, the motion to be simulated by the articulator includes vertical, lateral and protrusive jaw movements. Recent improvements in dental model articulators include making the articulator systems detachable from the casts to facilitate ease of working on the dental models. Exemplary of prior art patents that address detachability of articulator elements from the cast, and that further provide structure that facilitates the occlusal and masticatory motion are the present inventor's articulator systems taught in U.S. Pat. Nos. 4,382,787, 4,449,930, 4,734,033, and Des. 306,206. The tab cast mount, complemented by the ball and socket structural arrangement and the flexible and detachable hinged structure taught by the foregoing listed prior art patents, greatly facilitate proper alignment of the paired casts, and further facilitate the simulation of the paths of natural occlusal and masticatory registration of the paired dental model casts. However, while the prior art articulator systems have addressed the detachability and simulation of occlusal and masticatory registration of paired dental model casts, the prior art has not fully addressed the simulation of occlusal and masticatory registration of paired dental model casts where the dental models comprise irregular, or missing teeth structure in the back molar regions of one of the casts. This non-uniform dental model structure results in a vertically unsupported back molar bite region that frustrates the simulation of vertical masticatory, or back molar bite movement because vertical movement beyond a natural occlusal bite position is permitted by the prior art articulator structures. As a result of the non-uniform bite situation, the prior art articulator systems have resorted to improvised solutions that work with the basic articulator system. One such improvised solution is shown in FIG. 1, where the illustrated dental articulator system is shown functioning on paired dental model casts having a non-uniform molar region. As shown, a stop rod is utilized to prevent translational movement beyond the indicated spacing D in the toothless molar region between the opposing casts. This step involves having to prepare a cast to receive the stop rod which is fixedly positioned to the casts to stop the translational movement. This procedure, while preventing the undesired translational movement during the masticatory registration process, does so, after the situation is encountered, and after the models have been modified with the stop rod modification. This step is viewed as disruptive and inconvenient during the dental model registration process.

Although prior art patents do teach articulators having vertical post structure located near the back molar regions of the dental model casts, (see generally, U.S. Pat. Nos. 3,092,909, 3,808,689, 4,103,424, 4,299,570, 4,865,544 and 5,046,949), these vertical structures are not elements of an articulator system that solve the particular problem addressed by the present invention, i.e. to facilitate utilization of a dental articulator system on paired dental model casts having a non-uniform molar region. Further, these prior art articulators, that contain the vertical structures, lack including the widely accepted detachable and disposable structural characteristics, lack joinable joint structure that facilitates proper alignment of the paired casts in combination with hinged, flexible structure that facilitate the simulation of the paths of natural occlusal and masticatory registration of the paired dental model casts.

Therefore, a need is seen to exist for a dental model articulator that facilitates normal utilization on paired dental model casts having either uniform, or non-uniform back molar regions, and that is provided in an economical structure that facilitates being a disposable item. A need is also seen to exist for a dental model articulator which is further provided with structure that facilitates being multi-directionally maneuvered to achieve proper alignment of the paired casts, that is detachable and hinged to facilitate working on the teeth models and for simulation of the paths of natural occlusal and masticatory registration of the paired dental model casts.

SUMMARY OF THE INVENTION

Accordingly, the primary object of the present invention is to provide an improved and efficient dental articulator apparatus and method that facilitates normal utilization on paired dental model casts having either uniform, or non-uniform back molar regions.

Another object of the present invention is to provide an improved dental articulator having the above primary object structure that is also provided in an economical structure that facilitates being a disposable item.

Yet another object of the present invention is to provide an improved dental articulator having the above objects and that also provides structure that facilitates being multi-directionally maneuvered to achieve proper alignment of the paired casts, that is detachable and hinged to facilitate working on the teeth models and for simulation of the paths of natural occlusal and masticatory registration of the paired dental model casts.

The foregoing objects are accomplished by providing a dental articulator structure for use in registration of a pair of casts of a dental model which are positioned in an opposing and spaced relationship. In the broadest embodiment, the articulator structure includes at least one axially rigid support member having opposing ends from which joinable and jointed cast attachment members are orthogonally joined, and from which they extend for attachment to respective opposing casts. One of the cast attachment members being pivotably detachable from an end of the at least one axially rigid support member, and being fixedly attachable to one of the paired casts of the dental model. The other cast attachment member being fixedly attachable to the other one of the paired casts of the dental model and extending to, and orthogonally joined to the other end of the at least one axially rigid support member. The at least one axially rigid support member and the orthogonally joinable cast attachment members being structure that locates the axially rigid support member substantially close to the back molar ends of the opposing pair of dental model casts, such that translational movement of the dental model casts is prevented in a plane parallel to the axially rigid support member. Each of the orthogonally joinable cast attachment members being preferably formed as a two-piece joinable structure having a cast attachment end, and a support attachment end. The two-piece joinable structure that forms the cast attachment member has mating curved, partially spherical surfaces (quasi-(ball and socket) configuration) that, prior to being fixedly joined, facilitate multi-directional alignment of the pair of opposing dental model casts. The cast attachment members may be formed as a tandem structural arrangement that includes the two-piece joinable structure in combination with at least one spacer block that is useful for maintaining an orthogonal relationship between the at least one axially rigid support member and both of the cast attachment members and attached dental model casts. In a preferred embodiment, the at least one axially rigid support member is formed as a U-shaped structure defining a pair of axially rigid support arms. In use, and at an appropriate cast alignment step, the joinable surfaces are adhesively joined. The detachable structure facilitates independent cast attachment manipulation. The mating surfaces of the two-piece joinable structure, and the spacer blocks are provided with textured surfaces, such as a mesh pattern, or grooves, that facilitate the adhesive to wick and achieve a strong bond between the mating surfaces.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 3 is a top view of the present invention showing a tongue and groove type of alignment and mounting structure for securing the hinged cast attachment member to the upper dental model cast, and also illustrating the spherical (multi-directional) type of adjustment made possible by the joinable surfaces that are part of the two-piece cast attachment members.

FIG. 4 is a side view showing the dental model articulator of the present invention hingedly and detachably secured to both upper and lower dental model casts and illustrating the preferred close horizontal spacing relationship of the axially rigid support member and the adjacent dental model casts that prevents translational movement beyond the indicated spacing D in the toothless molar region between the opposing casts.

FIG. 5 is a perspective view showing the dental model articulator of the present invention hingedly and detachably secured to both upper and lower dental model casts and illustrating the desired protrusive and sideways flexibility of the articulator structure and the spacing D where translational movement is prevented.

DESCRIPTION OF THE PREFERRED EMBODIMENT

Figure 1:
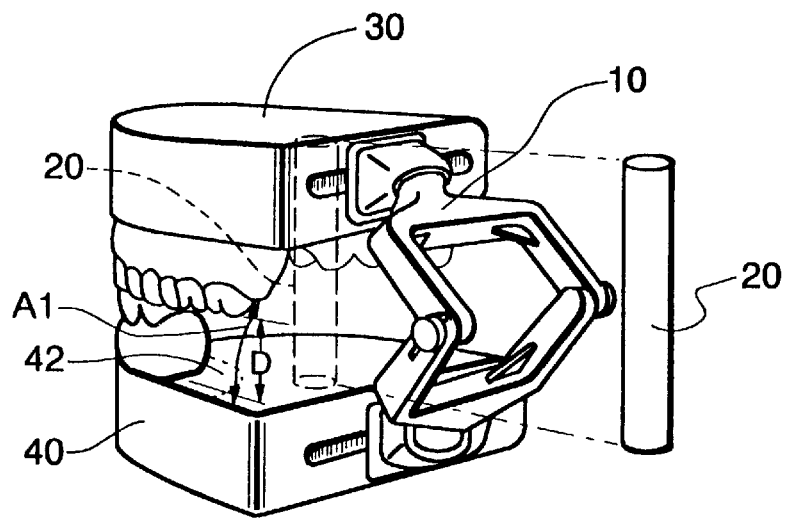
FIG. 1 illustrates a dental articulator wherein a stop rod must be utilized to prevent translational movement beyond the indicated spacing D in the toothless molar region between the opposing casts.
Figure 2:
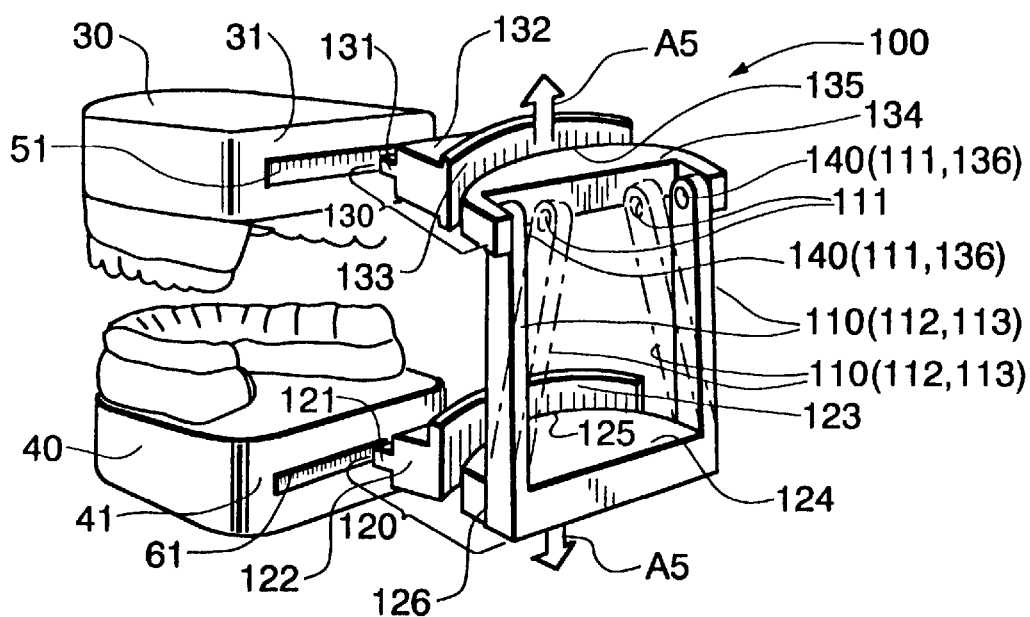
FIG. 2 is a perspective view of an embodiment of the present invention, illustrated in an unassembled state and positioned adjacent a pair of dental model casts that are to undergo initial alignment and subsequent registration, and also illustrating a U-shaped, two arm embodiment of the axially rigid support member having sideways flexing characteristics that also facilitates detachability from the cast attachment member.

As discussed previously, FIG. 1 illustrates a prior art dental articulator system 10 wherein a stop rod 20 must be utilized to prevent translational movement A1 beyond the indicated spacing D in the toothless molar region 42 between the opposing casts 30, 40. FIG. 2 shows dental articulator apparatus 100, designed according to the primary object of the present invention. Articulator 100 provides a solution that eliminates having to perform the step of placing a stop, such as stop rod 20, to prevent the translational movement A1 on dental model casts 30,40 having a toothless molar region, such as region 42 depicted in FIG. 1. As illustrated, articulator 100 is positioned adjacent a pair of dental model casts 30,40 that are to undergo initial alignment and subsequent registration. Articulator 100 is preferably formed from a disposable plastic material and includes, in the preferred embodiment, a U-shaped body, referred to as the axially rigid support member 110, having axially rigid arms 112, 113 that have sideways flexing characteristics that facilitate detachability from the upper cast attachment member 130. While articulator 100 is formed as a U-shaped structure, a single axially rigid support member, or other equivalent axially rigid structure is considered within the scope of the invention. Thus, as depicted in FIG. 2, articulator structure 100 includes two axially rigid support members, or arms 112, 113 having respective opposing ends from which joinable and jointed cast attachment members 120, 130 are orthogonally joined, and from which members 120, 130 extend for attachment to the back ends 31,41 of respective opposing casts 30, 40. Cast attachment member 130 is shown pivotably attachable at a pivot 140. By example, pivot 140 is facilitated by holes 111, at the upper end of each of the arms 112, 113, that detachably mate with pin shafts 136 formed on the support attachment end 137 of member 130. As depicted in FIG. 2, each of the orthogonally joinable cast attachment members 120, 130 are preferably formed as two-piece joinable structures (122,124), (132, 134), respectively, each having respective cast attachment ends 121, 131, and respective support attachment ends 126, 137. The two-piece joinable structures (122,124), (132,134) that form the cast attachment member 120, 130, have mating curved, partially spherical surfaces (123,125), (133,135) that, prior to being fixedly joined, facilitate multi-directional alignment, depicted by arrow A4 in FIG. 3 and by arrow A5 in FIG. 2.

It should be noted that, although casts 30,40 are herein provided having a toothless molar region 42 in the back part of the models, the present invention will function on dental models that have uniform teeth structures. The initial alignment of the dental model casts 30,40 is effected according to well known techniques in the art, and ultimately lead to the step of attaching the casts to the particular articulator to be employed for simulating the occlusal and masticatory motion. In the present invention, and by example only, the back face of casts 30, 40 are adapted with grooved ends 31, 41 having slots or grooves 51 and 61 for receiving tabs or tongues 121, 131 on attachment portions, or mounts 122, 132. FIG. 3 shows the alignment A3 made possible by the combined tongue and groove structures (51,131) for positioning the mount 132 to the upper cast 30. The attachment of mount 122 to the lower cast 40 is similarly effected, see FIG. 4 showing groove 61 mated with tongue 121. The cast mount portions 122, 132 are fixedly attachable to casts 30,40 using adhesives, such as the prefired fast setting cyanoacrylate or aerobic adhesive. Wicking grooves on cast 30, 40 may be employed, as illustrated and taught by the present inventor in U.S. Pat. Nos. Des. 302,725 and 4,734,033, to improve the cast-to-mount bond.

Once mounts 122,132 are fixedly attached to casts 30, 40, the support member attachment portions 124,134 of the cast attachment assemblies 120,130 are adhesively joined to mounts 122,132 after appropriate alignment as indicated by arrows A4 and A5 in FIGS. 2 and 3. In the preferred embodiment, support attachment portion 134 is an independent piece having pin shafts 136 at an end 137, and spherical surface 135 at the other end. Attachment portion 124 is formed integral with, and integrally interconnects arms 112, 113 at an end 126 and is provided with a spherical surface 125 at an opposing end. As noted above, portions (122,124) and (132,134) are formed to facilitate motion indicated by arrows A4 and A5 for aligning the casts and thus, are formed, as noted above, having partially spherical, joinable surfaces (123,125), (133,135), respectively. By example only, surfaces 123,133 are formed concave and surfaces 125,135 are formed convex. After determining the final orientation of the casts 30,40 and the desired placement of the articulator 100, surfaces (123,125) and (133,135) are adhesively joined to form joints 150, 160, respectively, see generally FIGS. 3, 4, 5. The formation of joints 150, 160 completes assembly of respective upper and lower jaw models.

In accordance with the primary object of the present invention, the distance depicted as Hs in FIGS. 3 and 4 is determined by the length of cast attachment members 120, 130, and is preferably kept to a minimum (preferable range 0.40 to 0.75 inches more preferably 0.50 to 0.75 inches) to assure that axially rigid support member 110 (112,113) are closely attached in a parallel spaced relationship with the back faces of opposing dental model casts 30, 40. The close spacing relationship Hs, in combination with the axially rigid structure of support 110 (112,113), assures that translational movement is prevented in the space depicted by the letter D in FIG. 4.

According to another object of the present invention, upper and lower jaws are hingedly and detachably secure at pivot 140, see generally FIG. 4 showing hinge action arrow A2., and FIG. 3 showing pivot 140 (111,136) at an upper end 110 of arms 112, 113. FIG. 5 is a perspective view showing the dental model articulator 100 hingedly and detachably secured to upper dental model cast 30 at pivot 140 (111,136) located at an upper end 110A of arms 112,113. Cast attachment member 130 (132,134) is shown as a two-piece structure joined at joint 150 (133,135) and being fixedly attached at tongue and groove joint formed by members 131,51, see also FIG. 4. Thus, cast attachment member 130 (FIG. 2) is pivotably detachable from a first distal end 110A of axially rigid support member 110 and fixedly attachable to cast 30. The angular relationship between cast attachment member 130, having cast 30 attached, and axially rigid support member 110 is preferably orthogonal. However, the particular alignment and registration requirements that result in the best bite for the particular dental model being simulated will determine the final adhesive fixation that forms joint 150.

The fixation of joint 150 is also related to the fixation of joint 160 for the lower cast 40 during the alignment process. As previously discussed, the lower cast attachment member 120 comprises attachment portion 124 that is integral with the axially rigid support arms 112,113. FIG. 5 shows arms 112, 113 being interconnected by attachment portion 124 at an end 110B opposite open end 110A, and also shows the spherical surface 125 joined with mating curved surface 123 to form joint 160. The shape of surface 123 of cast attachment portion 122 is preferably an elongated, concave, channel-like curved structure that facilitates convex spherical surface 125 having multi-alignment capability before being adhesively fixed to form joint 160. The shapes of surfaces 133,135 are similar and provide the same multi-alignment capability before forming joint 150. Thus, cast attachment member 120 is fixedly attachable to cast 40 and extends from a distal end 110B of axially rigid support member 110.

FIG. 5 also illustrates the primary object of the present invention, i.e. that the axially rigid construction of arms 112,113, in conjunction with the close spacing relationship Hs between the arms and the back face of the cast, (best seen in FIGS. 3 and 4), assures that translational movement is prevented in the spacing D about the region 42. Notwithstanding the axially rigid construction of arms 112,113, FIG. 5 also illustrates that articulator 100 is also constructed for facilitating the protrusive and sideways flexibility characteristics that are desirable in an articulator system. The flexible is generally indicated by flexing motion arrows F1, F2, and F3.

The flexing motion is facilitated by the arms 112 and 113 being spaced apart substantially vertically extending struts that provide torsional response to pressure to simulate the articulation of a patient's jaw movement as illustrated by direction indicating arrows F1, F2 and F3 and the directions in between. Thus, arms 112 and 113 are torsion response struts that are the sole suspending supports of the upper or top model cast 30 in contact with the lower stationary model cast 40. The struts 112 and 113 should be substantially completely relaxed and substantially free of torsional tension when the teeth of the model casts 30 and 40 are in their fully occluded positions.

For preferred action, and simplicity of construction, in one preferred embodiment, there are two spaced apart struts positioned substantially at the outermost one side of articulator 100 with the upper and lower respective model cast mounts 134 and 124 extending away therefrom and projecting in substantially common directions at substantially right angles from the struts to positions of securement to respective model casts 30 and 40 via adjustable connectors, i.e. dental model cast mounting blocks 132 and 122 respectively. In some embodiments it may be preferable to split each strut, or form other multiples of spaced struts. Of course, in addition, in some situations a center strut may be desirable at the side of articulator 100 from which the model cast mounts project. Generally, a single strut provides less preferred torsional properties, but an articulator with a single arm may advantageously provide the other advantages of the present invention fully.

To provide the desired torsional properties in the preferred embodiment depicted in FIGS. 2–5, the arms 112 and 113 are preferable injected molded from plastic, preferably thermoplastic or thermosetting plastics that are not brittle after polymerization and forming and/or shaping. The most preferred plastic is thermoplastic and preferably class 66 thermoplastic. The exemplary embodiment illustrated was formed of class 66, Vytel 10L thermoplastic available from Dupont Corporation. The support attachment portions of the dental model cast mounting blocks 122 and 123 are preferably made of the same plastic as the arms 112 and 113, as are the spacers 210 and the articulator cast mounts 124 and 134.

Each arm 112 and 113 preferably has a height extending 1.50 to 1.80 inches, more preferably 1.60 to 1.75 inches above the top surface of the lower articulator cast mount 124, each arm having a cross sectional dimension of preferably 0.12 by 0.18 inches, more preferably 0.125 to 0.188 inches. The height of the arms is measured to their outer top tips and the holes, or pin shafts 136 for the pivots are centered and are preferably 0.03 to 0.05 inches below the tips of the arms in the exemplary embodiment.

For the best torsion response, struts, or arms 112 and 113, in a preferred embodiment, will have a breadth dimension, in the direction of the projection of the model cast mounts 134 and 124, which is the direction of the arrow F1, that is greater (preferably 1½ times greater) than the width dimension which is the direction indicated by the arrow A4. Further, in a preferred embodiment the articulator 100 has arms 112 and 113 that are of substantially uniform dimension, i.e. width and breadth between the base mount 124 and their tips. These features are important in providing optimum simulation of masticating, as well as other movements to which a denture may be subjected to during use.

Preferably, the arms 112 and 113 should be within 1.0 to 1.2 inches, more preferably 1.0 to 1.125 inches of the nearest extent of the molar region of the model cast. The arms 112 and 113 are spaced apart 1.2 to 1.3 inches, more preferably 1.20 to 1.30 inches. This approximates the average spacing of the molar regions at the rear of arches of upper and lower dental model casts 30 and 40. This spacing aids in simulating the natural hinging of the human jaw. It will be noted that this positions the torsional response struts 112 and 113 within the usual width dimension of the dental model cast. In other words, the cast is normally wider than articulator 100.

The lower and upper support attachment portions, 122 and 132, are forward projecting dental model cast connectors and have respective cross sections of 0.4 by 0.5, more preferably 0.40 to 0.60 inches in the direction of arrow A5 in FIG. 2 and a width of 1.20 to 1.30, more preferably 1.245 to 1.255 inches in the direction of arrow F2 in FIG. 5. In horizonal extent, the convex curvature of the face of articulator cast mounts 124 and 134 and the concave curvature of joinable mounts 122 and 132 is preferably between 1.20 and 1.75 inches, more preferably 1.245 and 1.255 inches, and the preferred radiuses are 1.4 to 1.6 inches, more preferably 1.45 to 1.55 inches. While preferably the faces are portions of an evenly progressing circle, in some embodiments they can be elliptical, for example.

It will be observed that the lower face of the cast 40 in FIG. 5 is intended to sit on the work support surface or table and the articulator 100 is suspended in the preferred configuration. This is a preferred method of achieving the vertical relationship for articulation. It is preferred that the concave faces of the joinable mounts 122 and 132 have the greater perpendicular vertical extents, preferably 0.55 to 0.70 inches, more preferably 0.61 to 0.64 inches and that the convex faces of the articulator mounts 124 and 134 have lesser perpendicular vertical extents, preferably 0.22 to 0.26 inches, more preferably 0.24 to 0.25 inches to facilitate selecting a wide range of fixation location along arrow A5. Also, the convex faces 123,133 of articulator mounts 124 and 134 have a vertical curvature of 1.45 to 1.55 inches. Vertical surfaces 125,135 do not have a vertical curvature to facilitate being selectively fixed along the convex faces 123, 133, along arrow A5. While the terms upper and lower and horizontal and vertical have been used, these obviously refer to direction when the articulator is oriented in upright position.

The preferred plastic construction of articulator 100 results in realizing another object of the present invention, namely to provide an improved, economical dental articulator structure that facilitates being a disposable item.

Figure 6:
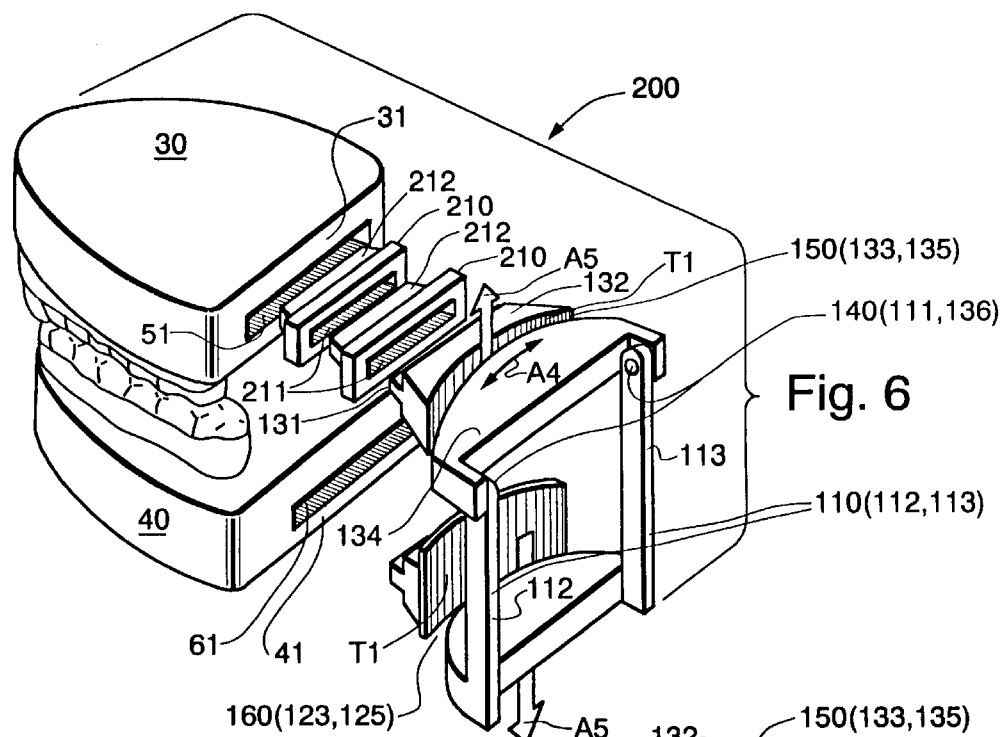
FIG. 6 is a perspective view of a variation of the present invention showing a tandem tongue and groove mounting arrangement for attaching to the upper cast which arrangement includes the two-piece joinable cast attachment member, shown in FIGS. 2–5, and (by example) two matable spacer blocks that facilitate placing the axially rigid support member in a parallel relationship with the back end of the dental model casts, and in a preferred orthogonal relationship with the assemblage referred to as cast attachment members.
Figure 7:
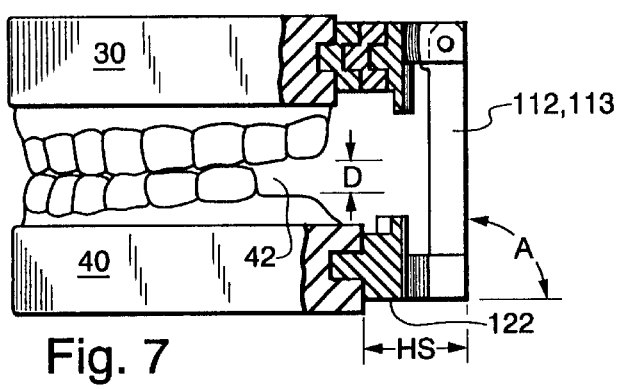
FIG. 7 is a side view, showing the embodiment depicted in FIG. 6 fully assembled with all joinable surfaces adhesively bonded, illustrating the spacing D where movement is prevented by the axially rigid support member, and further illustrating the tandem tongue and groove mounting arrangement of the spacer blocks with the two-piece cast attachment members that facilitate placing the axially rigid support member close to, and in parallel relationship with the back end of the attached cast, and in an orthogonal relationship with the cast attachment members.
Figure 8:
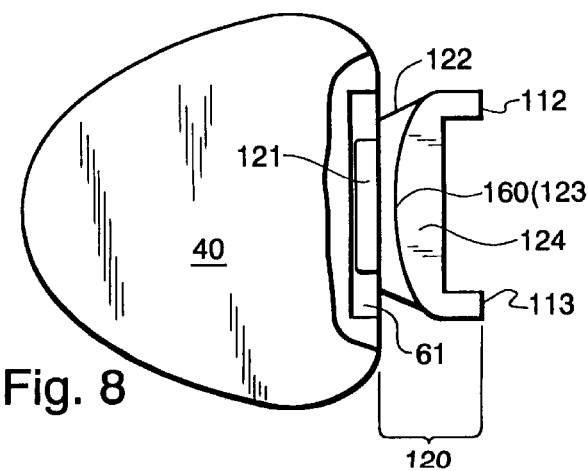
FIG. 8 is a bottom view of the dental model cast depicted in FIGS. 6 and 7 illustrating the use of only the two-piece cast attachment member, and further showing the support attachment end of the two-piece structure as being integral with bottom cross member of the U-shaped axially rigid support member.

FIG. 6 is a perspective view of an alternative dental articulator embodiment 200 of the present invention. Embodiment 200 satisfies in every respect the objects of the present invention. Notable structural variation include a tandem tongue and groove mounting arrangement 130A (see FIG. 9) for attaching to upper cast 30. The tandem arrangement 130A includes the two-piece joinable cast attachment members 132,134, (previously discussed and shown in FIGS. 2–5), and, by example, two matable spacer blocks 210. In this particular embodiment 200, the lower cast 40 is attached using similar pieces as used for embodiment 100, see FIGS. 7 and 8. The utilization of spacers 210 depends upon the relative alignment of the back faces of the opposing cast 30,40 during an initial alignment step. The relative alignment is a factor of the initial placement of the teeth models on the raw casts. Thus, a technician can select the number of spacers 210 needed for the task at hand to compensate for the cast's back face offset, and to assure that the axially rigid support member 110 is in a substantial orthogonal relationship with the assemblage referred to as cast attachment members 120,130, and also to minimize the spacing Hs, (see generally FIG. 7 showing angle A being substantially at 90 degrees and Hs). The resulting articulator structure is axially rigid along the longitudinal axis of arms 112,113 and prevents translational movement into the toothless region 42 and spacing D, see FIG. 7. Pivot 140 (111,136) facilitates hinge action of cast 30,40 a well as detachment of the casts 30,40 form each other.

Figure 9:
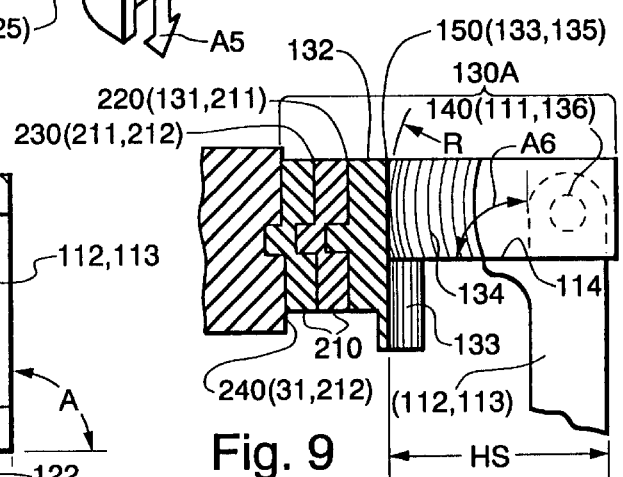
FIG. 9 is an enlarged view of the upper cast portion showing the hinged open end of the axially rigid support member, and the tandem structural arrangement of the spacers and the two-piece cast attachment member, which together form a composite, jointed cast attachment member structure. The composite structure being facilitated by the tongue and groove mating structure of the spacers and the curved spherical mating surfaces of the two-piece cast attachment member.
Figure 10:
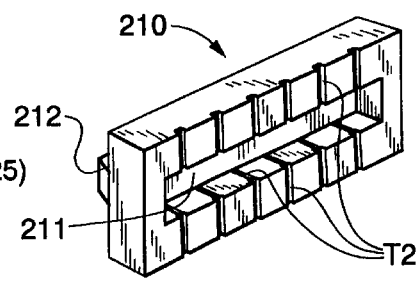
FIG. 10 is an enlarged perspective view of the spacer illustrating the tongue and groove structure, showing as well, the wicking grooves that help achieve a strong adhesive bond during an assembly step.

Joints 150 and 160 are formed after selecting a final alignment location, as previously discussed. However, the adhesive bonding is improved by texturing the surfaces (123,125) and (133,135). The texturing T1 is shown, by example, in a mesh pattern. Joints 150, 160 are enhanced by constructing surfaces 125 and 135 having a spherical radius R (approx. 1.5 inches) for producing better alignment and contact with mating surfaces 123, 135, see FIG. 9. FIG. 9 also shows shelf 114 on the upper end of arms 112,113 for limiting rotation A6 during an initial alignment involving support member attachment portion 134. The initial step of attaching to the cast differs from embodiment 100 in that a spacer 210 is mounted to the groove 41, employing a tongue 212 provided as part of the spacer structure, see FIG. 10. Spacer 210 is also provided with a groove 211 that is similar to groove 41 and is designed to mate with either tongue 212 or 131. Groove 211 facilitates the use of another similar spacer 210 to extend the reach and accomplish the desired articulator mounting objective. Spacer 210 is also textured about the groove area to provide improved wicking action of the adhesive used to form the tongue and groove joints 220 (131,211), 230 (211,212) and 240 (31,212), see FIG. 9. The texturing T2 is formed as wicking grooves that feed into the groove structure 211, see FIG. 10.

To use the articulator 100, slots 51 and 61 are cut or formed disposed horizontally in respective substantially flat planar surfaces at one side, ends 31 and 41, of dental model cast 30 and 40. The ends 31 and 41 extend substantially perpendicularly to the back of the arch of the set of teeth and are perpendicular in vertical extent.

Next, the area of each respective dental model cast 30 and 40, including the areas of the slots and of the flat faces of respective ends 31 and 41 adjacent to the slots 51 and 61 that are to be contacted by the cast mounting blocks are coated with an adhesive, preferably the fast setting cyanoacrylate adhesive, commercially available from KV33 Corporation under the brandname VERTEX Adhesive, Super Thin cyanoacrylate adhesive. The respective tongues 121 and 131 and adjacent planar flat faces of the cast mounting blocks that are to contact the coated areas of the dental model casts are then preferably coated respectively with the same adhesive and brought into engagement with respective coated areas of the dental model casts and adhesive is set by spraying the adhesive accelerator, or initiator, commercially available from KV33 Corporation under the brandname VERTEX Accelerator on the cyanoacrylate interface area to set the adhesive and freeze in position the mounting. This secures the respective parts firmly together. It will be understood that the tongues 121 and 131 are preferably sized to engage against the inside of slots 61 and 51, respectively, and be adhesively secured therein.

After the dental model casts 40 and 30 have been secured to respective cast mounting blocks 122 and 132 they are typically ready to be mounted to articulator 100. In a preferred procedure, the dental model casts 40 and 30 are placed in occlusion and the concave textured faces 123 and 133 of respective cast mounting blocks 122 an 132 are coated with cyanoacrylate adhesive. The respective textured convex faces 125 and 135 of the articulator cast mounts 124 and 134 of articulator 100 are coated with cyanoacrylate adhesive and the respective faces 123 and 125 and 133 and 135 are brought into interface contact and aligned horizontally and vertically so that when frozen, or set by the setting of the cyanoacrylate adhesive, the cast 40 will set substantially level on the flat table surface with the teeth of casts 40 and 30 in occlusion with struts 112 and 113 vertical and the articulator 100 substantially completely free of torsional stress as illustrated in FIG. 5. Then the adhesive accelerator, or initiator is sprayed on the cyanoacrylate interface areas to set the adhesive and set, or freeze the construction Articulation can then be carried out in conventional manner through the torsional stressing of struts 112 and 113 to simulate normal jaw movements of a patient. The upper cast 30 may be removed for better access by pushing the tips of the struts toward one another as illustrated in FIG. 2.

When the dental model cast assembled, with the cast mounting blocks, are not going to provide a proper at-rest articulation occlusion position, as determined either by, unadhered preassembly of the parts, or just trained-eye observation, spacer block 210 can be added, as clearly illustrated in FIGS. 6,7 and 9 to adjust the positions. The articulator spacer block 210 has two outwardly facing sides, a tongue 212 may be seen to project from one side, and groove, or slot 211, projects inwardly from the opposite side. Four walls disposed at substantially 90° from the planar face surrounding the slot penetrated into the block 210 to from the slot. A plurality of channel wicking grooves are formed in the planar face and extend to at least near the inner most extent of two of the penetrating walls that form the slot. This aids in good adhesive distribution and adherence. The slots 211 are sized to receive tongues 212 so that spacer blocks 210 can be built up as illustrated.

Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus.

I claim:

1. A dental model cast mounting block having a tongue projecting from one side for attachment to a dental model cast and a face on a reverse side that is concave in horizontal extent and perpendicular in vertical extent; said side from which said tongue projects having a substantially planar face except for said tongue, and said face being textured; an adhesive connection to a dental model cast; and an adhesive connection directly to an articulator model cast mount having a face that is convex in horizontal extent with a curvature matching that of the concave curvature of the face of the dental model cast mounting block and perpendicular in vertical extent providing a good interface contact between the dental model cast mounting block and the articulator model cast mount; further comprising an articulator spacer block wherein said adhesive connection is indirectly to said dental model cast through said articulator spacer block; said articulator spacer block comprising two opposite outwardly facing planar sides, one of said sides having a tongue projecting outwardly therefrom and the opposite of said sides having a slot projecting inwardly with said slot having four walls penetrating disposed at substantially 90° from said planar side with at least two of said slot walls and said one planar side having a plurality of channel grooves formed therein, extending from the outer edge of said planar said to at least near the inner most extent of at least two of said penetrating walls; the articulator spacer block being adhesively secured to said dental model cast and said tongue of said dental model cast mounting block being adhesively secured directly in said slot of said articulator spacer block.

2. The dental model cast of claim 1 wherein:

said concave side's concavity has an even radius of 1.45 to 1.55 inches.

3. The dental model cast mounting block of claim 1 said dental model cast comprising a set of teeth having an arch and having a substantially flat surface at one side extending substantially perpendicular to the back of the arch of the set of teeth and said substantially flat surface having a horizontally disposed slot formed therein, said tongue of said dental model cast mounting block being adhesively secured in said slot and said planar face of said dental model cast mounting block adhesively secured to said substantially flat surface of said dental model cast, said adhesive securement comprising fast setting cyanoacrylate adhesive and wherein said dental model cast mounting block and said articulator model cast mount comprise class 66 thermoplastic.

\* \* \* \* \*